US009950111B2

(12) United States Patent
Köhler et al.

(10) Patent No.: US 9,950,111 B2
(45) Date of Patent: Apr. 24, 2018

(54) DEVICE FOR THE TRANSCUTANEOUS, IN VIVO MEASUREMENT OF THE CONCENTRATION OF AT LEAST ONE ANALYTE IN A LIVING ORGANISM

(75) Inventors: Hans Köhler, Graz (AT); Ingo Klimant, Labuch (AT)

(73) Assignees: JOANNEUM RESEARCH FORSCHUNGSGESELLSCHAFT MBH, Graz (AT); TECHNISCHE UNIVERSITÄT GRAZ, Graz (AT)

( * ) Notice: Subject to any disclaimer, the term of this patent is extended or adjusted under 35 U.S.C. 154(b) by 1501 days.

(21) Appl. No.: 13/377,500

(22) PCT Filed: Jun. 2, 2010

(86) PCT No.: PCT/EP2010/057732
§ 371 (c)(1),
(2), (4) Date: Feb. 29, 2012

(87) PCT Pub. No.: WO2010/142590
PCT Pub. Date: Dec. 16, 2010

(65) Prior Publication Data
US 2012/0165625 A1    Jun. 28, 2012

(30) Foreign Application Priority Data
Jun. 9, 2009    (AT) .................................. A 891/2009

(51) Int. Cl.
*A61M 5/172*    (2006.01)
*A61B 5/145*    (2006.01)
(Continued)

(52) U.S. Cl.
CPC ......... *A61M 5/1723* (2013.01); *A61B 5/1459* (2013.01); *A61B 5/14532* (2013.01);
(Continued)

(58) Field of Classification Search
CPC ............ A61M 5/1723; A61M 5/31533; A61M 5/31565; A61B 5/00; A61B 5/0028;
(Continued)

(56) References Cited

U.S. PATENT DOCUMENTS 4,033,330 A * 7/1977 Willis ................ A61B 5/14539
356/39
5,246,867 A   9/1993 Lakowicz et al.
(Continued)

FOREIGN PATENT DOCUMENTS

AT    408182 B    9/2001
EP    0 221 005 A2   5/1987
(Continued)

*Primary Examiner* — Bradley J Osinski
*Assistant Examiner* — Nilay Shah
(74) *Attorney, Agent, or Firm* — Robert A. Blaha; Smith Tempel Blaha LLC

(57) ABSTRACT

A device for the transcutaneous, in vivo measurement of the concentration of at least one analyte in a living organism includes a catheter which can be introduced into the organism, and a luminescence indicator, which is immobilized on the catheter and which reacts to a change in the concentration of the at least one analyte to be measured with a change in at least one optical property. The luminescence indicator is transcutaneously connected to a source for providing an excitation radiation and a detector for detecting the measuring radiation. The luminescence indicator is immobilized on the outer circumference of the catheter, which is used to dispense a fluid medium, for example a medication, into the organism or to drain a body fluid.

15 Claims, 2 Drawing Sheets

(51) Int. Cl.
  *A61B 5/1455* (2006.01)
  *A61B 5/1459* (2006.01)
  *A61B 5/00* (2006.01)

(52) U.S. Cl.
  CPC ...... *A61B 5/14539* (2013.01); *A61B 5/14542* (2013.01); *A61B 5/14556* (2013.01); *A61B 5/415* (2013.01); *A61M 2005/1726* (2013.01); *A61M 2205/3306* (2013.01); *A61M 2230/201* (2013.01); *A61M 2230/205* (2013.01); *A61M 2230/208* (2013.01)

(58) Field of Classification Search
  CPC .............. A61B 5/0084; A61B 5/14539; A61B 5/14546; A61B 5/4881; A61B 5/1451; A61B 5/14556; A61B 5/14555; A61B 5/14542; A61B 5/14549; A61B 5/14532
  See application file for complete search history.

(56) References Cited

U.S. PATENT DOCUMENTS

| | | | |
|---|---|---|---|
| 5,383,466 A * | 1/1995 | Partika | A61B 8/0833 600/459 |
| 5,628,310 A * | 5/1997 | Rao | A61B 5/0017 600/317 |
| 6,011,984 A * | 1/2000 | Van Antwerp | A61B 5/14532 600/310 |
| 6,032,059 A | 2/2000 | Henning et al. | |
| 6,304,766 B1 | 10/2001 | Colvin, Jr. | |
| 2006/0263839 A1 | 11/2006 | Ward et al. | |
| 2008/0269723 A1 * | 10/2008 | Mastrototaro | A61B 5/14865 604/890.1 |
| 2009/0088615 A1 | 4/2009 | Robinson et al. | |
| 2015/0223742 A1 * | 8/2015 | Hajnsek | A61B 5/6852 600/347 |

FOREIGN PATENT DOCUMENTS

| | | | | |
|---|---|---|---|---|
| IL | WO 2008114218 A2 * | 9/2008 | ........ | A61M 5/14244 |
| WO | 9625089 A1 | 8/1996 | | |
| WO | 9636275 A1 | 11/1996 | | |
| WO | 2006102412 A2 | 9/2006 | | |
| WO | WO 2006124759 A2 | 11/2006 | | |
| WO | WO 2009021064 A1 | 2/2009 | | |

\* cited by examiner

DEVICE FOR THE TRANSCUTANEOUS, IN VIVO MEASUREMENT OF THE CONCENTRATION OF AT LEAST ONE ANALYTE IN A LIVING ORGANISM

TECHNICAL FIELD

This invention relates to a device for transcutaneous, in vivo measurement of the concentration of at least one analyte in a living organism with a carrier introducable into the organism and, immobilized on the carrier, a luminescence indicator which reacts on a change of the concentration of the analyte to be measured with a change in at least one optical property, wherein the luminescence indicator is transcutaneously in connection with a source for providing the excitation radiation and a detector for acquisition of the measurement radiation.

BACKGROUND

For patients who have to permanently monitor the concentration of a specific analyte in the body and provide to the body medicaments for adapting this analyte to physiological values, a considerable effort arises.

So, for example patients with diabetes have to measure multiple times a day the blood glucose which is used as a basis for a therapy decision. In doing so, the skin is perforated for example with a lancet and the thereby emerging blood is applied on a measuring strip as part of a measuring system. After availability of the measurement value the insulin dose is calculated wherein the insulin is injected into the fat tissue by means of a needle. This measurement/injection cycle is associated with two skin penetrations causing pain. Further, the insulin is administered in a "non-physiological" dosage. For optimizing the uniform dosage, insulin pumps have been developed which continuously deliver the insulin through an implantable catheter. Besides the advantage of the continuous delivery of the insulin, the pump catheter may reside in the tissue for a longer time, whereby a multiple piercing is omitted and the inconveniences associated therewith can be avoided.

From AT 408.182 B there is known a glucose sensor in which by means of a setting needle a catheter is brought into the tissue of a living organism. After the positioning of the catheter in the tissue the setting needle is retracted and replaced by a tube-like carrier with an electrochemical sensor. The sensor is located at the outer periphery of the tube-like carrier in the region of a wall opening of the catheter inserted into the tissue such that a measurement contact to the surrounding tissue can be established. The electrical supply line of the sensor is conducted in an annular gap between the tube-like carrier and the catheter outwardly to an evaluation unit. The inside lumen of the tube-like carrier as well as the annular channel between the tube-like carrier and the catheter is respectively connected with a syringe pump by means of which liquids can be brought into the tissue. Therefore in an insulin administration with this device, for measurement and application only one skin penetration is necessary.

From WO 96/36275 there is known a method and a device for transcutaneous measurement of an analyte in living tissue, in which a fluorescence indicator immobilized in a carrier tissue is implanted in the tissue. As carrier is used a planar or cylindrical membrane, for example a cellulose membrane permeable for glucose. The membrane comprises a tissue compatible fluorescence indicator which reacts on a change in the glucose concentration with a change in its fluorescence decay time or with a frequency shift. The excitation radiation is irradiated through the tissue from an outside located light source and the emerging measurement radiation gets through the tissue and the skin to an outside located detector the signals of which are supplied to an evaluation and display device. The administration of a medicament however is, due to the implanted sensor device, neither intended nor possible such that for example for an insulin administration an additional skin penetration would be necessary.

Further, a series of applications is known (see e.g. US 2009/0088615 A1), in which in vivo glucose measurements are carried out with a light guide insertable into the tissue, wherein different applications are described by means of which the measurement radiation can be separated from the excitation radiation.

Further, from WO 2006/102412 A2 a device is known which comprises an insulin pump and an apparatus for glucose measurement. Implementation variants are described in which, on an infusion canula for a medicament, electrochemical measurement apparatuses consisting of reference electrodes and counter electrodes are attached for measuring, after insertion of the canula into the tissue, an analyte concentration. According to a further implementation variant an electrochemical sensor with several electrodes is implemented as small as possible and is wound around the outer periphery of the catheter insertable into the tissue. All these implementation variants are technically very laborious, increase the diameter of the tissue canula and impair the quality of the surface of the canula, thereby hindering insertion into the tissue.

SUMMARY

It is an object of the invention to suggest, based on the known solutions for the measurement of an analyte and the delivery of a medicament into the organism, improvements admitting an non-traumatic treatment at low costs of the device.

This object is solved according to the invention in that the luminescence indicator is immobilized at an outer periphery (outer circumference) of a catheter which serves for delivery of a liquid medium, for example of a medicament, into the organism or for sucking up a body fluid. As a catheter there is adopted a thin one-time needle, for example made of steel or plastic, as used e.g. in the insulin therapy.

The invention combines e.g. the application of a medicament with the measurement of an analyte concentration in a way that the outside for example of a tissue catheter is coated with a luminescence-optical indicator. The analyte-specific answer of the luminescence indicator is detected by means of a detector at the skin surface and the analyte concentration is calculated. In an advantageous way the excitation of the luminophor and the measurement of the luminescence radiation is effected non-invasive as electromagnetic radiation through the tissue, wherein no terminals as for electrochemical sensors or light guides for optical sensors have to be brought into the tissue. Advantages are also present compared to WO 96/36725 cited to the prior art, in which the fluorescence indicator together with the carrier matrix is implanted. Herewith, an additional effort is associated for example with the removal of the implanted sensor at the end of the service life.

The device according to the invention may also be used for sucking up of a body fluid. For example, wound liquid may be sucked up from a surgery wound and at the same time on the outside of the catheter the oxygen concentration be measured as indicator of the local supply of the tissue. Thereby an indirect conclusion on the wound healing process may be obtained.

By immobilizing the luminescence indicator directly on the infusion catheter, the luminescence indicator is removed from the body automatically with the removal of the catheter. Besides the common transcutaneous access for measurement and medicament application or the extraction of body fluid, a further advantage is that the system can be manufactured extremely cost efficient since solely the catheter with the coating has to be exchanged, the remaining unit with electronics, optics, etc. is however usable several times.

In accordance with the invention the catheter may comprise at its outer periphery for example an annular recess or etching or roughening, respectively, for reception of the luminescence indicator being existent preferably in a carrier layer.

It is also possible to immobilize the luminescence indicator in at least one segment of the catheter by physical fixation or chemical bonding. The segment coated with the luminescence indicator is in direct contact with the body fluid wherein the coating of the catheter may take place also partially (e.g. one-sided). The segment includes a larger area for counterbalancing punctual inhomogeneities of the to be measured analyte concentration in the organism.

A particular simple application of the device according to the invention is provided by an implementation variant in which the catheter is located projecting outwardly in a base element of a housing wherein the base element is capable of being placed onto the surface of the organism under insertion of the catheter.

Further according to the invention it is intended that in the housing an electronic unit is present which controls the provision of the excitation radiation and the detection of the measurement radiation, calculates the analyte concentration and/or determines a medicament dose depending on the analyte concentration. Further the electronic unit may control the dosage unit for the medicament and apply the beforehand determined medicament dose preferably automatically into the organism.

In particular, the herein disclosed subject matter includes the following embodiments:

In an example embodiment, a device for transcutaneous in vivo measurement of the concentration of at least one analyte in a living organism, is disclosed. The device comprises a carrier insertable into the organism and, immobilized on the carrier, a luminescence indicator which reacts on a change of the concentration of the analyte to be measured with a change of at least one optical characteristic. Moreover, the luminescence indicator is transcutaneously connected with a source for providing the excitation radiation and a detector for detecting the measurement radiation, characterized in that the luminescence indicator is immobilized at the outer periphery of a catheter serving for delivery of a liquid medium, for example a medicament, into the organism or for sucking up a body fluid.

In an embodiment, the luminescence indicator of the device is immobilized in at least one segment of the catheter by physical fixation or chemical bonding.

In another embodiment, the catheter has at its outer periphery a recess or an etching for reception of the luminescence indicator which is existent preferably in a carrier layer.

In still another embodiment, the device according to one of the above embodiments is characterized in that the device has a dosage unit for a medicament connected with the catheter. The medicament dose is adjustable preferably depending on the analyte concentration measured by the luminescence indicator.

In yet another embodiment, the device according to one of the above embodiments is characterized in that the catheter is positioned outwardly protruding in a base element of a housing. The base element can be placed onto the surface of the organism under insertion of the catheter.

In still another embodiment, the device according to the previous embodiment is characterized in that the housing houses the source for providing the excitation radiation, the detector for detecting the measurement radiation, and the dosage unit for delivery of a medicament.

In another embodiment, the device according to either of the previous two embodiments is characterized in that there is existent in the housing an electronic unit which controls the provision of the excitation radiation and the detection of the measurement radiation, calculates the analyte concentration, and determines, depending on the analyte concentration, a medicament dose.

In still another embodiment, the device according to the previous embodiment is characterized in that the electronic unit controls the dosage unit for the medicament and applies the determined medicament dose preferably automatically into the organism.

In yet another embodiment, the device according to one of the previous embodiments is characterized in that the analyte to be measured is an endogenous metabolite, for example glucose or lactate, or an exogenously administered substance.

BRIEF DESCRIPTION OF THE DRAWINGS

In the following, the invention is described in more detail on the basis of schematic drawings. There is shown in.

DETAILED DESCRIPTION

In the following, under the term "luminescence indicator" is understood not only a dye flourescating or phosphorescating after excitation but also a coating which receives the dye in a functional matrix material.

Figures 1, 2:
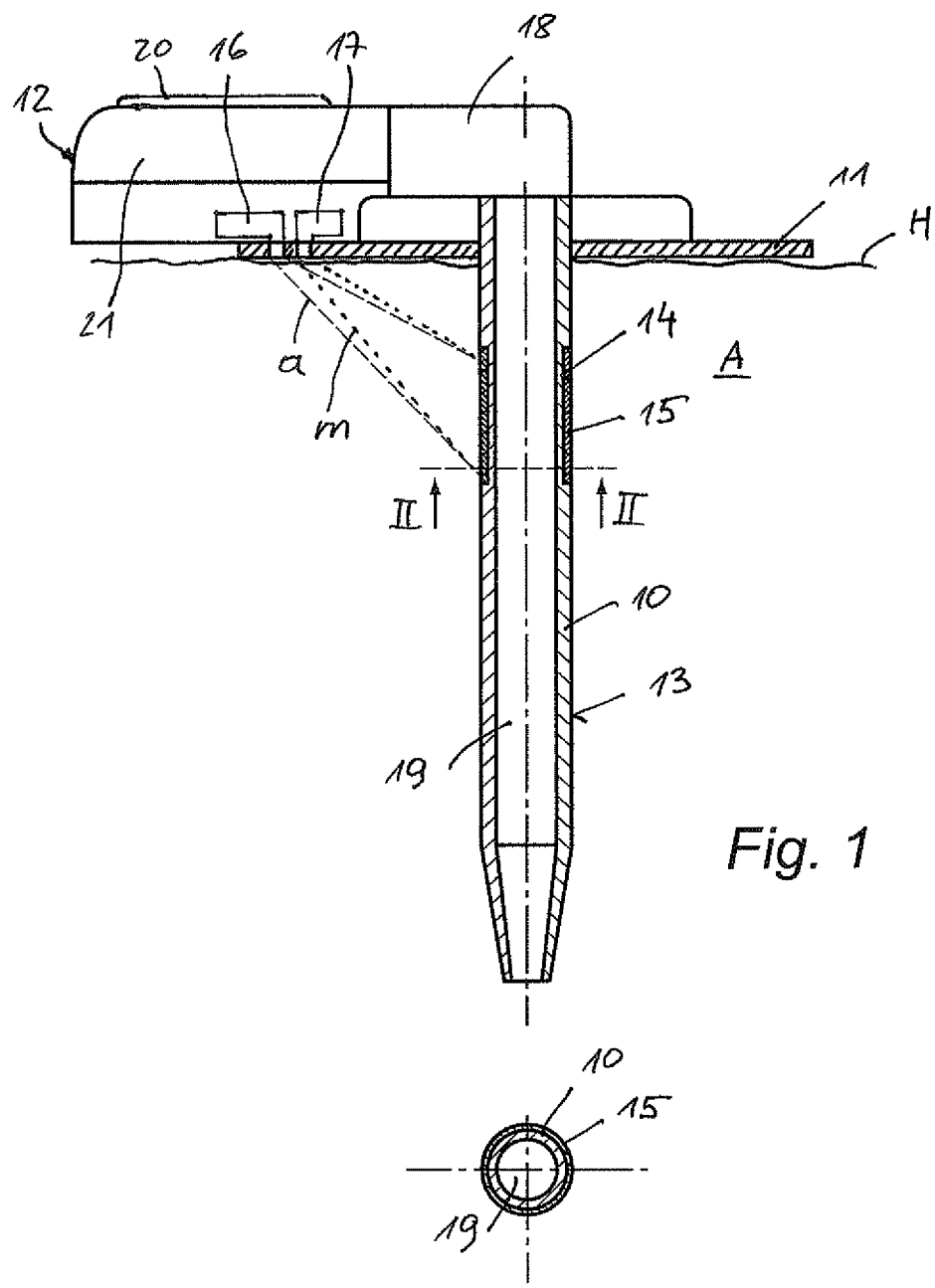
FIG. 1 a first implementation variant of the invention in a partial sectional view, FIG. 2 a sectional view according to line II-II in FIG. 1, FIG. 3 a simplified implementation variant of the device according to the invention in a sectional view, as well as FIG. 4 a schematic view of the individual functional components of the device according to the invention.

The device according to the invention, shown in FIGS. 1 and 2, for transcutaneous in vivo measurement of the concentration of an analyte (e.g. Glucose) in the tissue of an organism A with a skin surface H comprises a catheter 10, pierceable into the tissue, which is located protruding outwardly in a base element 11 of a housing 12 of the device. The catheter 10 comprises at the outer periphery 13 an annular recess or etching 14 for reception of the luminescence indicator 15 preferably being existent in a carrier layer.

The housing 12 of the device receives a source 16 for providing the excitation radiation a and a detector 17 for detection of the measurement radiation m. In order to avoid disturbing absorptions in the tissue, the excitation radiation and the measurement radiation should lie in a range of about 600 nm to 1100 nm.

In the example shown, in the housing is provided a dosage unit 18 for delivery of a medicament (e.g. insulin) which is connected to the lumen 19 of the canula 10.

Due to the immobilization of the luminescence indicator 15 in an annular recess 14 of the canula 10, a smooth, flat surface of the canula 10 can be maintained without having to increase the outer periphery 13.

In the housing 12 of the device, there is further located an electronic unit 21 which determines, depending on the analyte concentration measured by the luminescence indicator 15, a medicament dose which can be preferably automatically applied into the organism A. The electronic unit 21 also serves for controlling the measurement process for calculating the analyte concentration.

Figure 3:
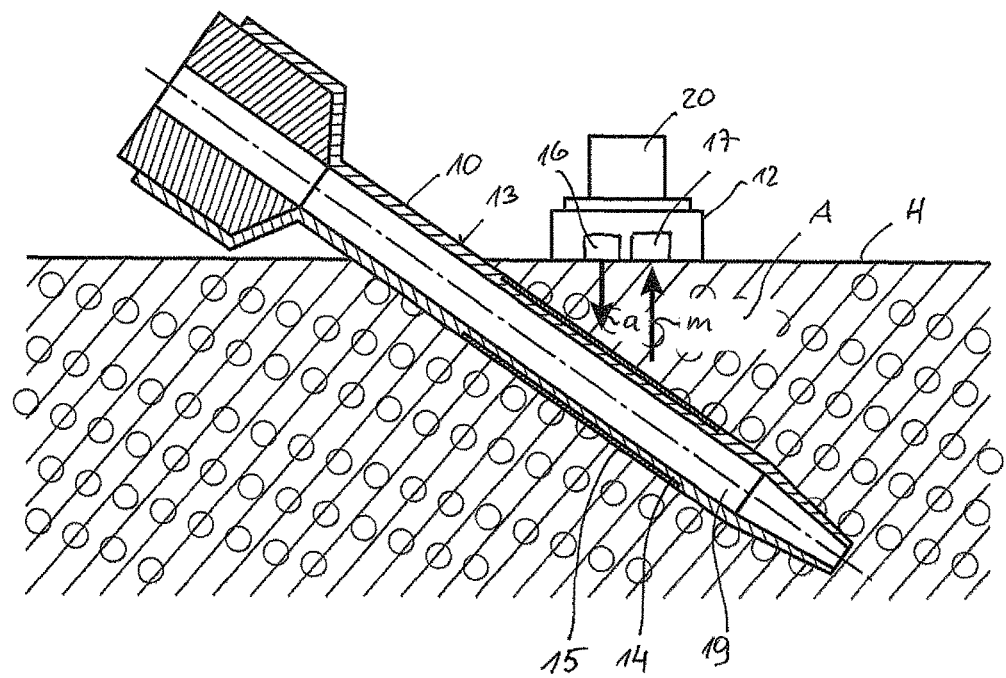

The implementation variant according to FIG. 3 shows a device according to the invention in which the catheter 10 for the delivery of a medicament into the organism A and the housing 12, which houses the excitation source 16 and the detector 17, are separate units. In this implementation the housing 12 has to be put on the skin surface H of the organism A in the vicinity of the inserted catheter 10, for stimulating the luminescence indicator 15 through the tissue and to detect the measurement radiation m. For example, a common insulin pump may be employed wherein the measurement values are transmitted from the measurement unit to the insulin pump by hand or automatically (via cable or radio signal).

Figure 4:
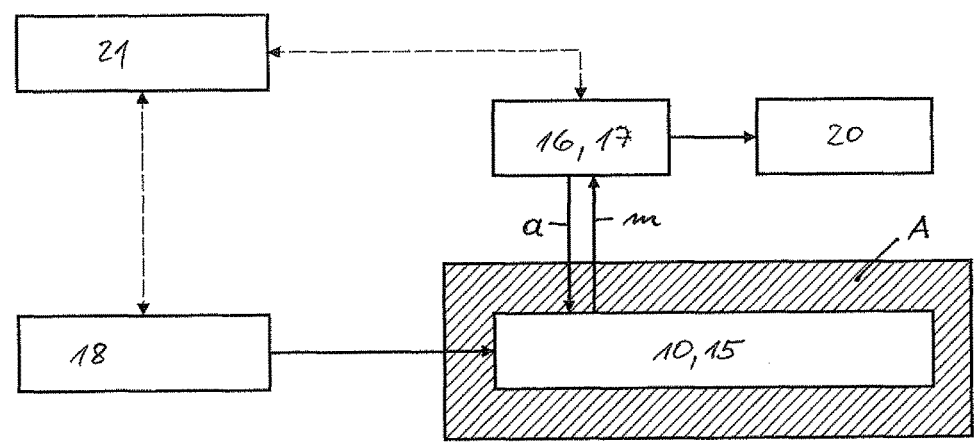

FIG. 4 shows in a schematic view the individual functional components of the device according to the invention. The catheter 10 with the luminescence indicator 15, introduced into the organism A, is connected with the outside unit having source 16 and detector 17 only via the excitation radiation and measurement radiation a, m. A dosage unit 18 controlled by the electronic unit 21 applies the calculated medicament dose over the catheter 10 into the tissue. All measurement values and dosage specification may be presented at a display unit 20.

The device according to the invention is well suited for determination of the tissue glucose and the administration of the necessary insulin amounts, but may however also be used for measurements in different body fluids like blood, lymph, brain liquid or other.

Besides glucose also lactate, oxygen, pH, electrolyte or another endogenous or an exogenously administered substance can be measured.

As medicaments, insulin or insulin analoga, but also glucagon, GLP (glucagon-like peptide), growth hormones, etc. may be administered.

The device according to the invention may be employed in the human medicine as well as in the veterinary medicine.

The invention claimed is:

1. A device for transcutaneous in vivo measurement of a concentration of at least one analyte in a living organism, the device comprising:
    a catheter insertable into the organism; and
    a luminescence indicator which reacts on a change of the concentration of the at least one analyte to be measured with a change of at least one optical characteristic, wherein the luminescence indicator is transcutaneously connected with a source for providing an excitation radiation and a detector for detecting a measurement radiation, wherein the luminescence indicator is immobilized at an outer periphery of the catheter serving for delivery of a liquid medium, into the organism or for sucking up a body fluid;
    wherein the luminescence indicator is immobilized in at least one segment of the catheter by physical fixation or chemical bonding;
    wherein the catheter is positioned outwardly protruding from a base element of a housing wherein the base element is capable of being placed onto a surface of the organism upon insertion of the catheter.

2. The device according to claim 1, wherein the catheter has at its outer periphery a recess or an etching for reception of the luminescence indicator.

3. The device according to claim 2, wherein the luminescence indicator is existent in a carrier layer.

4. The device according to claim 1, further comprising:
    a dosage unit for a medicament connected with the catheter, wherein a medicament dose is adjustable.

5. The device according to claim 4, wherein a housing houses the dosage unit.

6. The device according to claim 4, wherein the medicament dose is adjustable depending on the analyte concentration measured by the luminescence indicator.

7. The device according to claim 1, further comprising:
    a dosage unit; and
    an electronic unit which controls the provision of the excitation radiation and the detection of the measurement radiation, calculates the analyte concentration, and determines, depending on the analyte concentration, a medicament dose.

8. The device according to claim 7, wherein the electronic unit controls the dosage unit for a medicament and applies the determined medicament dose into the organism.

9. The device according to claim 1, wherein the at least one analyte to be measured is one of an endogenous metabolite or an exogenously administered sub stance.

10. The device according to claim 1, wherein the liquid medium is a medicament.

11. A device for transcutaneous in vivo measurement of a concentration of at least one analyte in a living organism, comprising:
    a catheter insertable into the organism;
    a luminescence indicator which reacts on a change of the concentration of the at least one analyte to be measured with a change of at least one optical characteristic,
    wherein the luminescence indicator is transcutaneously connected with a source for providing an excitation radiation and a detector for detecting a measurement radiation,
    wherein the luminescence indicator is immobilized at an outer periphery of the catheter serving for delivery of a liquid medium into the organism or for sucking up a body fluid;
    wherein the luminescence indicator is immobilized in at least one segment of the catheter by physical fixation or chemical bonding;
    wherein the catheter is positioned outwardly protruding from a base element of a housing wherein the base element is capable of being placed onto a surface of the organism upon insertion of the catheter, the housing supporting the source for providing the excitation radiation and the detector for detecting the measurement radiation; and
    an electronic unit in the housing which controls the provision of the excitation radiation and the detection of the measurement radiation, calculates the analyte concentration, and determines, depending on the analyte concentration, a medicament dose.

12. The device according to claim 11, wherein the electronic unit controls the dosage unit for the medicament and applies the determined medicament dose automatically into the organism.

13. The device according to claim 11, wherein the liquid medium is a medicament.

14. A device for transcutaneous in vivo measurement of a concentration of at least one analyte in a living organism, the device comprising:
- a catheter insertable into the organism; and
- a luminescence indicator which reacts on a change of the concentration of the at least one analyte to be measured with a change of at least one optical characteristic,
- wherein the luminescence indicator is transcutaneously connected with a source for providing an excitation radiation and a detector for detecting a measurement radiation,
- wherein the luminescence indicator is immobilized at an outer periphery of the catheter serving for delivery of a liquid medium into the organism or for sucking up a body fluid;
- wherein the luminescence indicator is immobilized in at least one segment of the catheter by physical fixation or chemical bonding;
- the catheter having at its outer periphery a recess or an etching for reception of the luminescence indicator;
- wherein the catheter is positioned outwardly protruding from a base element of a housing wherein the base element is capable of being placed onto a surface of the organism upon insertion of the catheter; and
- wherein the housing houses the source for providing the excitation radiation and the detector for detecting the measurement radiation.

15. The device according to claim 14, wherein the liquid medium is a medicament.

* * * * *